US 8,699,688 B2

United States Patent
Wellons et al.

(10) Patent No.: US 8,699,688 B2
(45) Date of Patent: *Apr. 15, 2014

(54) NETWORK BASED HEALTHCARE INFORMATION SYSTEMS

(75) Inventors: David L. Wellons, Marietta, GA (US); Diane Brown Turcan, Smyrna, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 1529 days.

This patent is subject to a terminal disclaimer.

(21) Appl. No.: 11/903,900

(22) Filed: Sep. 25, 2007

(65) Prior Publication Data
US 2008/0028030 A1 Jan. 31, 2008

Related U.S. Application Data

(63) Continuation of application No. 10/253,500, filed on Sep. 24, 2002, now Pat. No. 7,298,836.

(51) Int. Cl.
*H04M 7/00* (2006.01)

(52) U.S. Cl.
USPC ..................................... 379/219; 379/220.01

(58) Field of Classification Search
USPC .................. 379/219, 220.01, 142.06, 265.09, 379/265.12, 265.13; 705/3; 709/206
See application file for complete search history.

(56) References Cited

U.S. PATENT DOCUMENTS

| | | | |
|---|---|---|---|
| 4,817,130 A | 3/1989 | Frimmel, Jr. | |
| 4,979,206 A | 12/1990 | Padden et al. | |
| 5,062,103 A | 10/1991 | Davidson et al. | |
| 5,062,133 A | 10/1991 | Melrose | |
| 5,113,429 A | 5/1992 | Morley, Jr. et al. | |
| 5,278,955 A | 1/1994 | Forte et al. | |
| 5,283,856 A | 2/1994 | Gross et al. | |
| 5,418,628 A | 5/1995 | Perkins | |
| 5,559,855 A | 9/1996 | Dowens et al. | |
| 5,619,991 A | 4/1997 | Sloane | |
| 5,651,058 A | 7/1997 | Hackett-Jones et al. | |
| 5,678,179 A | 10/1997 | Turcotte et al. | |
| 5,711,297 A | 1/1998 | Iliff | |
| 5,748,100 A | 5/1998 | Gutman et al. | |
| 5,764,731 A | 6/1998 | Yablon | |
| 5,815,566 A | 9/1998 | Ramot et al. | |

(Continued)

OTHER PUBLICATIONS

Unknown, "Can your healthcare services be improved by more effective call answering?", 2 pages.

(Continued)

*Primary Examiner* — William Deane, Jr.
(74) *Attorney, Agent, or Firm* — Scott P. Zimmerman, PLLC

(57) ABSTRACT

Methods, systems, and products are disclosed for enabling an exchange of electronic healthcare messages. An electronic message is received from a sender's address that is destined for a recipient's address. The electronic message may have an attached object associated with a sender's legacy system. The sender's address and the recipient's address are associated to a list of health care participant addresses. When both the sender's address and the recipient's address are matched to the list of health care participant addresses, then the electronic message is sent to a rule-based engine. When the sender's address and the recipient's address do not match the list of health care participant addresses, then an identifier is received that associates the electronic message with another legacy system and with a non-participant legacy system.

20 Claims, 9 Drawing Sheets

(56) References Cited

U.S. PATENT DOCUMENTS

| | | |
|---|---|---|
| 5,822,418 A | 10/1998 | Yacenda et al. |
| 5,841,854 A | 11/1998 | Schumacher et al. |
| 5,867,821 A | 2/1999 | Ballantyne et al. |
| 5,868,669 A | 2/1999 | Iliff |
| 5,878,130 A | 3/1999 | Andrews et al. |
| 5,915,010 A | 6/1999 | McCalmont |
| 5,917,893 A | 6/1999 | Katz |
| 5,924,074 A | 7/1999 | Evans |
| 5,930,759 A | 7/1999 | Moore et al. |
| 5,940,740 A | 8/1999 | Aas et al. |
| 5,946,659 A | 8/1999 | Lancelot et al. |
| 5,951,645 A | 9/1999 | Goto |
| 5,963,864 A | 10/1999 | O'Neil |
| 6,006,206 A | 12/1999 | Smith et al. |
| 6,018,713 A | 1/2000 | Coli et al. |
| 6,035,021 A | 3/2000 | Katz |
| 6,052,442 A | 4/2000 | Cooper et al. |
| 6,075,787 A | 6/2000 | Bobeck et al. |
| 6,088,429 A | 7/2000 | Garcia |
| 6,088,677 A | 7/2000 | Spergeon |
| 6,112,183 A | 8/2000 | Swanson et al. |
| 6,119,108 A | 9/2000 | Holmes et al. |
| 6,122,485 A | 9/2000 | Archer |
| 6,137,524 A | 10/2000 | Chea |
| 6,137,876 A | 10/2000 | Wong et al. |
| 6,151,586 A | 11/2000 | Brown |
| 6,185,603 B1 | 2/2001 | Henderson et al. |
| 6,201,804 B1 | 3/2001 | Kikinis |
| 6,206,829 B1 | 3/2001 | Iliff |
| 6,229,888 B1 | 5/2001 | Miloslavsky |
| 6,282,565 B1 | 8/2001 | Shaw et al. |
| 6,295,551 B1 | 9/2001 | Roberts et al. |
| 6,305,007 B1 | 10/2001 | Mintz |
| 6,310,543 B1 | 10/2001 | Yoshioka et al. |
| 6,324,279 B1 | 11/2001 | Kalmanek et al. |
| 6,339,593 B1 | 1/2002 | Kikinis |
| 6,366,658 B1 | 4/2002 | Bjornberg et al. |
| 6,374,229 B1 | 4/2002 | Lowrey et al. |
| 6,408,068 B1 | 6/2002 | Larson et al. |
| 6,411,947 B1 | 6/2002 | Rice et al. |
| 6,434,121 B1 | 8/2002 | Davidson et al. |
| 6,445,784 B2 | 9/2002 | Uppaluru et al. |
| 6,456,594 B1 | 9/2002 | Kaplan et al. |
| 6,462,656 B2 | 10/2002 | Ulrich et al. |
| 6,473,404 B1 | 10/2002 | Kaplan et al. |
| 6,482,156 B2 | 11/2002 | Iliff |
| 6,501,562 B1 | 12/2002 | Nakagiri et al. |
| 6,532,489 B1 | 3/2003 | Merchant |
| 6,561,809 B1 | 5/2003 | Lynch et al. |
| 6,603,847 B1 | 8/2003 | Griffith |
| 6,611,590 B1 | 8/2003 | Lu et al. |
| 6,631,271 B1 | 10/2003 | Logan |
| 6,633,848 B1 | 10/2003 | Johnson et al. |
| 6,674,403 B2 | 1/2004 | Gray et al. |
| 6,680,999 B1 | 1/2004 | Garcia |
| 6,721,412 B1 | 4/2004 | Youngs |
| 6,771,173 B1 | 8/2004 | Clayton et al. |
| 6,785,380 B2 | 8/2004 | Ribera |
| 6,810,429 B1 | 10/2004 | Walsh et al. |
| 6,859,649 B1 | 2/2005 | Denenberg et al. |
| 6,888,927 B1 | 5/2005 | Cruickshank et al. |
| 6,892,083 B2 | 5/2005 | Shostak |
| 6,898,625 B2 | 5/2005 | Henry et al. |
| 6,970,548 B2 | 11/2005 | Pines et al. |
| 6,996,406 B2 | 2/2006 | Lection et al. |
| 7,023,979 B1 | 4/2006 | Wu et al. |
| 7,167,553 B2 | 1/2007 | Shaffer et al. |
| 7,191,221 B2 | 3/2007 | Schatz et al. |
| 7,327,756 B2 | 2/2008 | Hamlin |
| 7,376,470 B2 | 5/2008 | Tanaka |
| 7,376,704 B2 | 5/2008 | Wellons et al. |
| 7,672,003 B2 | 3/2010 | Dowling et al. |
| 2002/0004727 A1 | 1/2002 | Knaus et al. |
| 2002/0010679 A1 | 1/2002 | Felsher |
| 2002/0016818 A1 | 2/2002 | Kirani et al. |
| 2002/0049615 A1* | 4/2002 | Huber .................. 705/3 |
| 2002/0055917 A1 | 5/2002 | Muraca |
| 2002/0055967 A1 | 5/2002 | Coussement |
| 2002/0068575 A1 | 6/2002 | Agrawal et al. |
| 2002/0076026 A1 | 6/2002 | Batten |
| 2002/0080416 A1 | 6/2002 | Quine |
| 2002/0106071 A1 | 8/2002 | Uppaluru et al. |
| 2002/0112008 A1 | 8/2002 | Christenson et al. |
| 2002/0114278 A1 | 8/2002 | Coussement |
| 2002/0120687 A1 | 8/2002 | Diacakis et al. |
| 2002/0143876 A1 | 10/2002 | Boyer et al. |
| 2002/0144154 A1 | 10/2002 | Tomkow |
| 2002/0163572 A1 | 11/2002 | Center, Jr. et al. |
| 2002/0167935 A1 | 11/2002 | Nabkel et al. |
| 2002/0188689 A1* | 12/2002 | Michael .................. 709/206 |
| 2003/0009530 A1 | 1/2003 | Philonenko et al. |
| 2003/0028399 A1 | 2/2003 | Davis et al. |
| 2003/0055684 A1 | 3/2003 | Jaskolski et al. |
| 2003/0058838 A1 | 3/2003 | Wengrovitz |
| 2003/0065738 A1 | 4/2003 | Yang |
| 2003/0135565 A1 | 7/2003 | Estrada |
| 2003/0135624 A1 | 7/2003 | McKinnon et al. |
| 2003/0191665 A1 | 10/2003 | Fitzgerald et al. |
| 2003/0191685 A1 | 10/2003 | Reese |
| 2003/0200226 A1 | 10/2003 | Wells et al. |
| 2003/0208543 A1 | 11/2003 | Enete et al. |
| 2004/0057569 A1 | 3/2004 | Busey et al. |
| 2004/0059603 A1 | 3/2004 | Brown, Jr. et al. |
| 2004/0117215 A1 | 6/2004 | Marchosky |
| 2004/0125938 A1 | 7/2004 | Turcan et al. |
| 2004/0153511 A1 | 8/2004 | Maynard et al. |
| 2004/0193449 A1 | 9/2004 | Wildman et al. |
| 2004/0203906 A1 | 10/2004 | Kato et al. |
| 2004/0249776 A1 | 12/2004 | Horvitz et al. |
| 2005/0035862 A1 | 2/2005 | Wildman et al. |
| 2005/0065817 A1 | 3/2005 | Mihai et al. |
| 2005/0097176 A1 | 5/2005 | Schatz et al. |
| 2005/0154792 A1 | 7/2005 | Deryugin et al. |
| 2005/0209891 A1 | 9/2005 | Jacobus et al. |
| 2007/0037605 A1 | 2/2007 | Logan |
| 2012/0106728 A1 | 5/2012 | Ghaffari et al. |

OTHER PUBLICATIONS

Unknown, "MediCall Offered by BellSouth", 34 pages.
NEC, Fusion Certification Announcement, Oct. 24, 2000, 3 pages.
Xtend, "PC Based Computer Telephony Integration Solutions", 9 pages.

* cited by examiner

NETWORK BASED HEALTHCARE INFORMATION SYSTEMS

CROSS REFERENCE TO RELATED APPLICATIONS

This application is a continuation of U.S. application Ser. No. 10/253,500, filed Sep. 24, 2002 and entitled "Network Based Healthcare Information Systems", now issued as U.S. Pat. No. 7,298,836, and incorporated herein by reference in its entirety.

NOTICE OF COPYRIGHT PROTECTION

A portion of the disclosure of this patent document and its figures contain material subject to copyright protection. The copyright owner has no objection to the facsimile reproduction by anyone of the patent document or the patent disclosure, but the copyright owner otherwise reserves all copyrights whatsoever.

BACKGROUND OF THE INVENTION

1. Field of the Invention

This invention generally relates to computer networks and to telephony. More particularly, this invention is directed to methods and systems for more efficient and effective communication and processing of electronic healthcare data in a telecommunications network-based healthcare information system.

2. Description of the Related Art

In *Epidemics*, Hippocrates wrote "[t]he art of medicine has three factors: the disease, the patient and the physician." Were he writing today, the Father of Medicine would also likely include "access to healthcare information" as a fourth factor. Why? Because today's healthcare marketplace is driven by increasing pressure for cost controls, by the increased strength of the consumer voice, by a shift from hospital inpatient care towards primary, ambulatory, and home care, by an emphasis on "case management," by increased competition, and by the focus on quality that is necessary for better patient care. This relentless drive to improve efficiencies and cut costs makes many traditional procedures inefficient. This relentless drive also presents great opportunities for healthcare professionals, organizations, and patients to enter into new types of multi-institution partnerships (e.g., strategic alliances between physician's offices, hospitals, clinics, labs, diagnostic centers, medical record repositories, insurers, patients, pharmaceutical and surgical suppliers, other vendors, etc.) that utilize many different computing systems and other communications technologies to manage and share electronic healthcare information. One of the biggest barriers facing these multi-institution partnerships is creating and maintaining an integrated delivery system (IDS) that facilitates an information-exchange of standardized or otherwise compatible data so that each participant in the partnership has efficient and effective access to the information.

Thousands, if not hundreds of thousands or more, of electronic documents, emails, and proprietary information are generated each day and shared among these multi-institution partnerships. For example, a physician might order a complex lab test from the local hospital. Instead of waiting on the results to arrive by hand delivery, the physician's office may get online and requests it via secure, encrypted email. The hospital's lab staff either manually attaches the lab result to a return email, or, in more advanced systems, the lab system responds automatically to the request and returns the results to a legacy system accessible by the physician. Another example is when a physician needs to admit a patient to the hospital. Instead of having the staff call the admission office and spend upwards of thirty (30) minutes talking and waiting on hold, the office sends the pre-admission information electronically, including patient record information and pre-admission orders to the hospital via an email attachment or directly to the hospital's legacy system. As used herein, the term "legacy systems" includes data processing, storage, management, and information systems, such as, for example, electronic patient health history, patient insurance information, demographic information, and physical records. Typically, the legacy systems are customized in terms of software, hardware, and network configuration for each participant of the multi-institution partnership. Typically, the legacy system includes a network of multiple computer systems; however, the legacy system may also be a stand-alone computer system.

In both of the above examples, the shared healthcare information may be processed in a variety of ways. For example, the hospital may provide information to the physician by transmitting healthcare data over a Local Area Network (LAN) connection into a database on a web server. This healthcare information could then be transmitted to the physician's computer system over a data connection, such as the Internet, Intranet or Extranet, or over a direct connection, such as dial up access, using push technology that automatically broadcasts the data to the physician's computer system and allows the physician to view the transmitted healthcare data using an appropriate software package, such as a browser. While the goal of the IDS interface of an information-exchange system is to translate and reformat the healthcare information from one legacy system so that it is compatible with another legacy system(s), thus far, the IDS systems have been primarily limited to very specialized healthcare information and limited in the features and services offered between linked legacy systems.

In addition to the challenges of implementing a successful IDS that enables the exchange of electronic healthcare information, most of the participants in the multi-institution partnerships must also comply with a variety of federal, state, local and other rules that protect the privacy and security of healthcare information associated with a patient. For example, the Health Insurance Portability and Accountability Act (HIPAA), signed into law by President Clinton on Aug. 21, 1996 (Pub. L. 104-191, 110 Stat. 1936), covers health plans, healthcare clearinghouses, and healthcare providers who conduct certain financial and administrative transactions (e.g., electronic billing and funds transfers) electronically. Providers (e.g., physicians, hospitals, etc.) and health plans are required to give patients a clear written explanation of how a covered entity may use and disclose a patient's healthcare information. Further, healthcare providers are required to obtain patient consent before sharing information for treatment, payment, and healthcare operations. In addition, HIPPA also requires that a provider adopt and implement privacy procedures to ensure the privacy and security of the healthcare information.

The above discussion illustrates how the sharing of healthcare information and technology are creating a new foundation for a virtual healthcare setting. With this emerging virtual healthcare setting, what are needed are improved network-based healthcare information systems that build communications infrastructures to support different organizational needs and capitalize on emerging trends in the healthcare setting. Accordingly, network-based healthcare information systems and components are needed that enable multiple legacy systems to share, transfer, and/or access standardized or otherwise compatible data of the various participants in the multi-institution partnership. Further, a need exists to improve notification, access, and management of the electronically shared healthcare information without investing millions of dollars in computer equipment, in a networking infrastructure, in maintenance, and in training while also complying with security, authenticity, and/or privacy requirements.

BRIEF SUMMARY OF THE INVENTION

The aforementioned problems and others are reduced by a telecommunications network-based healthcare information system (NBHIS). The NBHIS comprises systems and methods that leverage the assets of a telecommunications network to facilitate improved access, sharing, notification, security, and/or management of electronic healthcare data exchanged between or among different legacy systems. Some advantages of NBHIS include increased ability of each participant to flexibly manage and categorize electronic healthcare data that is exchanged with other participants, provide faster access to electronic healthcare data, and utilize a local proprietary network to reduce or prevent electronic healthcare data from entering traffic in a public data network, such as the Internet.

An embodiment of this invention describes a method that includes receiving electronic healthcare data associated with a sender's legacy system, interpreting the electronic healthcare data according to a rule-based engine to categorize the electronic healthcare data, and processing the electronic healthcare data into a receiver's legacy system. The sender's legacy system and the receiver's legacy system are associated with an integrated delivery system that enables an exchange of selected electronic healthcare data between one or more networks of communications devices associated with a telecommunications service provider. In a preferred embodiment, a rule-based application dataserver is used to categorize the electronic healthcare data. The rule-based application dataserver allows a customer (e.g., a participant) to control access, sharing, notification, security, and/or management of electronic healthcare data exchanged between or among different legacy systems. Typically, the rule-based application dataserver is associated with a central office ("CO"), a mobile telephone switching center ("MTSO"), or a combination CO/MTSO.

Another embodiment describes a method for communicating electronic healthcare data to a rule-based application dataserver associated with a telecommunications facility and allowing a customer (e.g., a participant) to manage the rule-based application dataserver including one or more databases associated with a rule-based profile. Similar to the first embodiment described above, the sender's legacy system and the receiver's legacy system are associated with an integrated delivery system that enables an exchange of selected electronic healthcare data between one or more networks of communications devices associated with a telecommunications service provider.

Another embodiment describes a method for establishing a data connection between a sender legacy system and a receiver legacy system that uses a rule-based application dataserver, communicating electronic healthcare data via the data connection, and allowing a customer to manage the rule-based application dataserver including one or more databases associated with a rule-based profile. The rule-based application dataserver is provided by a telecommunications provider and controls access between the sender legacy system and the receiver legacy system. Typically, the electronic healthcare data includes an electronic healthcare message having an attached object, a transaction reply, a transaction notification, a compatible object, and/or other electronic communications.

Another embodiment describes a system for remotely managing electronic healthcare data shared between different legacy systems communicating via a telecommunications connection that uses a rule-based application dataserver associated with a telecommunications facility. The system includes a network of interconnected communications devices serviced by a telecommunications service provider and a rule-based application dataserver for managing the exchange of electronic healthcare data between different legacy systems connected with the communications devices. The system further includes an application program, referred to herein as a NBHIS Management Module, that is installed in a customer's communications device, such as a computer system. The NBHIS Management Module provides an interface for the customer to remotely manage NBHIS Management Services including the rule-based application dataserver and its databases.

BRIEF DESCRIPTION OF THE SEVERAL VIEWS OF THE DRAWINGS

The above and other embodiments, objects, uses, advantages, and novel features of this invention are more clearly understood by reference to the following description taken in connection with the accompanying figures, wherein.

DETAILED DESCRIPTION OF THE INVENTION

Figure 1:
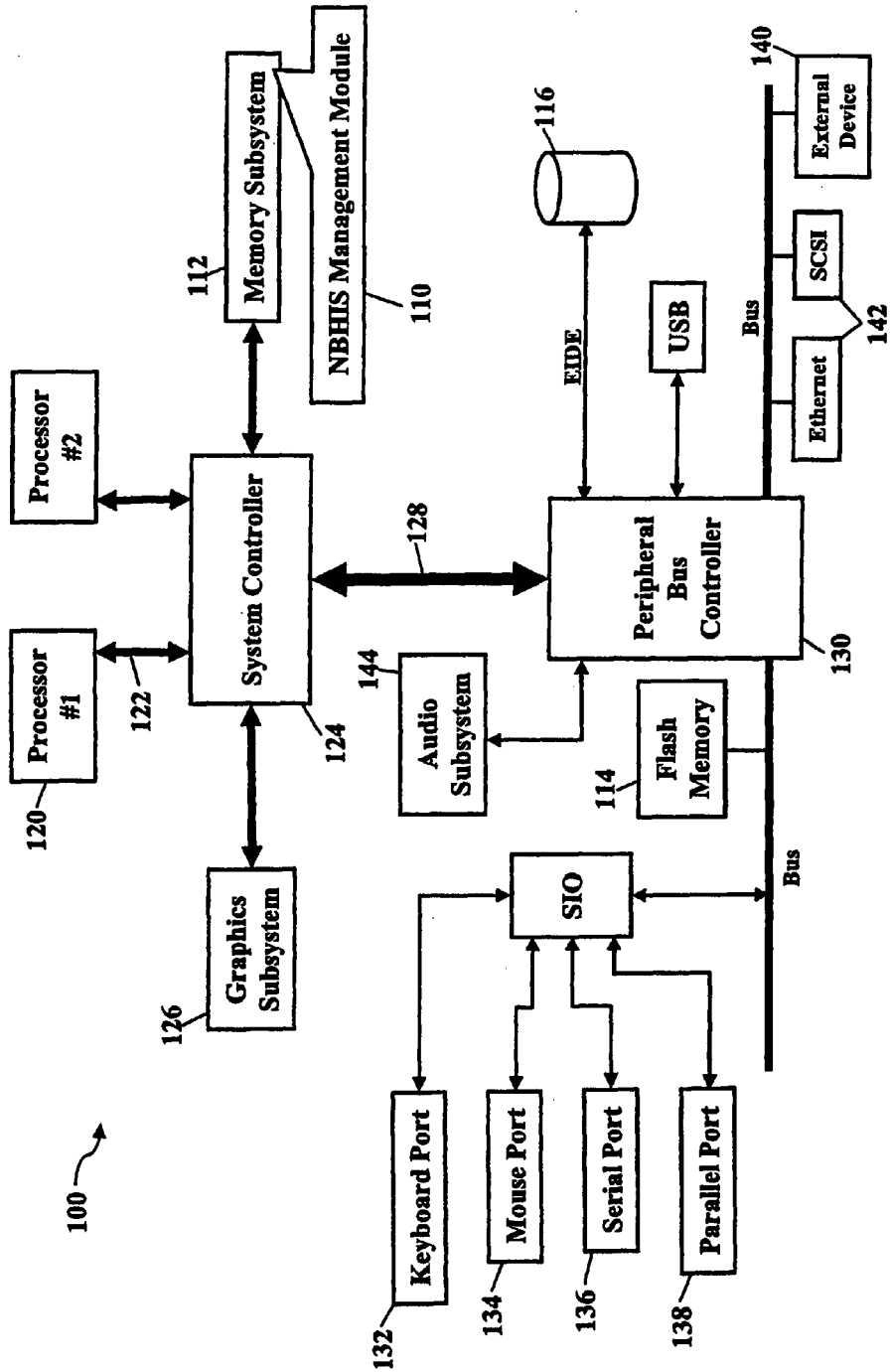
FIG. 1 is a block diagram showing of a NBHIS Management Module that resides in a computer system according to an embodiment of this invention.

This invention now will be described more fully hereinafter with reference to the accompanying drawings, in which exemplary embodiments are shown. This invention may, however, be embodied in many different forms and should not be construed as limited to the embodiments set forth herein;

rather, these embodiments are provided so that this disclosure will be thorough and complete, and will fully convey the scope of the invention to those of ordinary skill in the art. Moreover, all statements herein reciting embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, flowcharts, and the like represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular named manufacturer.

A telecommunications network-based healthcare information system (NBHIS) is typically a subject-specific group of related client, vendor, and service-oriented participants that leverage the assets of a telecommunications network. The purpose of NBHIS is to efficiently share information, automate business processes, and enhance market position. In the case of a healthcare NBHIS, participants may include a local hospital, insurance companies, HMOs, affiliated hospitals, clinics, physicians' offices, medical schools, universities, and strategic partners. Patients, as well as vendors, could also be included, as could service providers, such as clinical laboratories, pharmacy services, temporary agencies, private ambulance services, and subspecialty services. After all, rapid communication and exchange of information between these participants can make a critical difference in the quality of patient care. In most cases, each participant usually has its own legacy systems, including software, hardware, equipment, networks, and/or other information technology assets. For example, a hospital commonly has a local and/or a wide area network that utilizes Ethernet, dedicated private lines, Frame Relay, ISDN, ATM, ADSL, and the like. Further, these legacy systems provide an interface to a data network, such as the Internet, Intranet, and/or Extranet, that may be locally or remotely accessed by a participant's user (e.g., a hospital employee using a computer system within the hospital's legacy system).

This invention provides improved access, sharing, notification, routing, security, and/or management of electronic healthcare data exchanged between or among different legacy systems. These legacy systems are associated with a rule-based application dataserver provided by a telecommunications service provider. These legacy systems are also associated with an integrated delivery system (IDS) that uses associated rules, fields, and/or files to process exchanged information into a selected legacy system. As used herein, the term "electronic healthcare data" includes electronic healthcare messages such as email, attached objects (e.g., an attached file to the email), and compatible objects (e.g., an attached object that has been processed by the rule-based application dataserver and the IDS to format and/or standardize electronic information shared between a first and a second legacy system). The term "electronic healthcare data" also includes transaction notifications and/or transaction replies generated by the rule-based application dataserver and/or the IDS, and/or other means of communicating electronic information between or among NBHIS participants.

Referring now to the figures, FIG. 1 is a block diagram showing a NBHIS Management Module 110 residing in a computer system 100. The NBHIS Management Module 110 operates within a system memory device. The NBHIS Management Module 110, for example, is shown residing in a memory subsystem 112. The NBHIS Management Module 110, however, could also reside in flash memory 114 or peripheral storage device 116. The computer system 100 also has one or more central processors 120 executing an operating system. The operating system, as is well known, has a set of instructions that control the internal functions of the computer system 100. A system bus 122 communicates signals, such as data signals, control signals, and address signals, between the central processor and a system controller 34 (typically called a "Northbridge"). The system controller provides a bridging function between the one or more central processors 120, a graphics subsystem 126, the memory subsystem 112, and a PCI (Peripheral Controller Interface) bus 128. The PCI bus 128 is controlled by a Peripheral Bus Controller 130. The Peripheral Bus Controller 130 (typically called a "Southbridge") is an integrated circuit that serves as an input/output hub for various peripheral ports. These peripheral ports could include, for example, a keyboard port 132, a mouse port 134, a serial port 136 and/or a parallel port 138 for a video display unit, one or more external device ports 140, and networking ports 142 (such as SCSI or Ethernet). The Peripheral Bus Controller 130 could also include an audio subsystem 144.

The processor 120 is typically a microprocessor. Advanced Micro Devices, Inc., for example, manufactures a full line of ATHLON™ microprocessors (ATHLON™ is a trademark of Advanced Micro Devices, Inc., One AMD Place, P.O. Box 3453, Sunnyvale, Calif. 94088-3453, 408.732.2400, 800.5128.8450, www.amd.com). The Intel Corporation also manufactures a family of X86 and P86 microprocessors (Intel Corporation, 2200 Mission College Blvd., Santa Clara, Calif. 95052-8119, 408.765.8080, www.intel.com). Other manufacturers also offer microprocessors. Such other manufacturers include Motorola, Inc. (1303 East Algonquin Road, P.O. Box A3309 Schaumburg, Ill. 60196, www.Motorola.com), International Business Machines Corp. (New Orchard Road, Armonk, N.Y. 10504, (914) 499-1900, www.ibm.com), and Transmeta Corp. (3940 Freedom Circle, Santa Clara, Calif. 95054, www.transmeta.com).

The preferred operating system is WINDOWS® (WINDOWS® is a registered trademark of Microsoft Corporation, One Microsoft Way, Redmond Wash. 98052-6399, 425.882.8080, www.Microsoft.com). Other operating systems, however, are also suitable. Such other operating systems would include the UNIX® operating system (UNIX® is a registered trademark of the Open Source Group, www.opensource.org), the UNIX-based Linux operating system, WINDOWS NT®, and Mac® OS (Mac® is a registered trademark of Apple Computer, Inc., 1 Infinite Loop, Cupertino, Calif. 95014, 408.996.1010, www.apple.com).

The system memory device (shown as memory subsystem 112, flash memory 114, or peripheral storage device 116) may also contain an application program. The application program cooperates with the operating system and with a video display unit (via the serial port 136 and/or the parallel port 138) to provide a GUI for the NBHIS Management Module 110. The GUI typically includes a combination of signals communicated along the keyboard port 132 and the mouse port 134. The GUI provides a convenient visual and/or audible interface with the customer or user of the computer system 100. As is apparent to those of ordinary skill in the art, the selection and arrangement of the NBHIS Management Module 110 to manage NBHIS Management Services may be programmed over a variety of alternate mediums, such as, for example, a voice-activated menu prompt, an interactive session with an telecommunications network administrator, and the like.

The NBHIS Management Module 110 allows a user to manage NBHIS Management Services, such as: (1) allowing the user to customize rules and user groups associated with a rule-based engine of the rule-based dataserver including an access agent, a security agent, a messaging agent, a transaction agent, and a troubleshooting agent; (2) allowing the user to customize presentation, features, and/or management of an incoming electronic healthcare message (e.g., an email, an attached object, a compatible object, a transaction reply, a transaction notification, and/or other electronic communications); and (3) allowing the user to control the telecommunications network and/or a data network connection with his/her legacy system. For example, the user may select an Access Agent having a user group list to add, delete, or modify participant information, such as, associated service node addresses, IP addresses, email addresses, and/or other electronic address information associated with each NBHIS participant. An address of the user group list is associated with an incoming electronic healthcare message (shown as reference numeral 240 in FIG. 2) and acts as a trigger (similar to decoding an ICLID signal for telecommunication special service features offered by telecommunication service providers) to send the electronic healthcare message to a NBHIS rule-based application dataserver (shown as reference numeral 258 in FIG. 2). The NBHIS Management Module 110 also allows the user to customize features, such as electronic healthcare message handling options. For example, the NBHIS Management Module may split a user's screen into two viewing areas and present the incoming electronic healthcare message in one portion and present information associated with an attached object and/or a compatible object that has been or that might be integrated into the user's legacy system. Further, the NBHIS Management Services may allow the user to control whether to accept, decline, or postpone integration of the compatible object into the user's legacy system or might be set to automatically accept, decline, or postpone integration depending on a sending participant's address. Finally, the NBHIS Management Module 110 of the computer system may provide the IP address or the like so that the telecommunications network and/or the data network can communicate the electronic healthcare message, and, thus integrate telephony events and data network events with the user's computer system.

Figure 2:
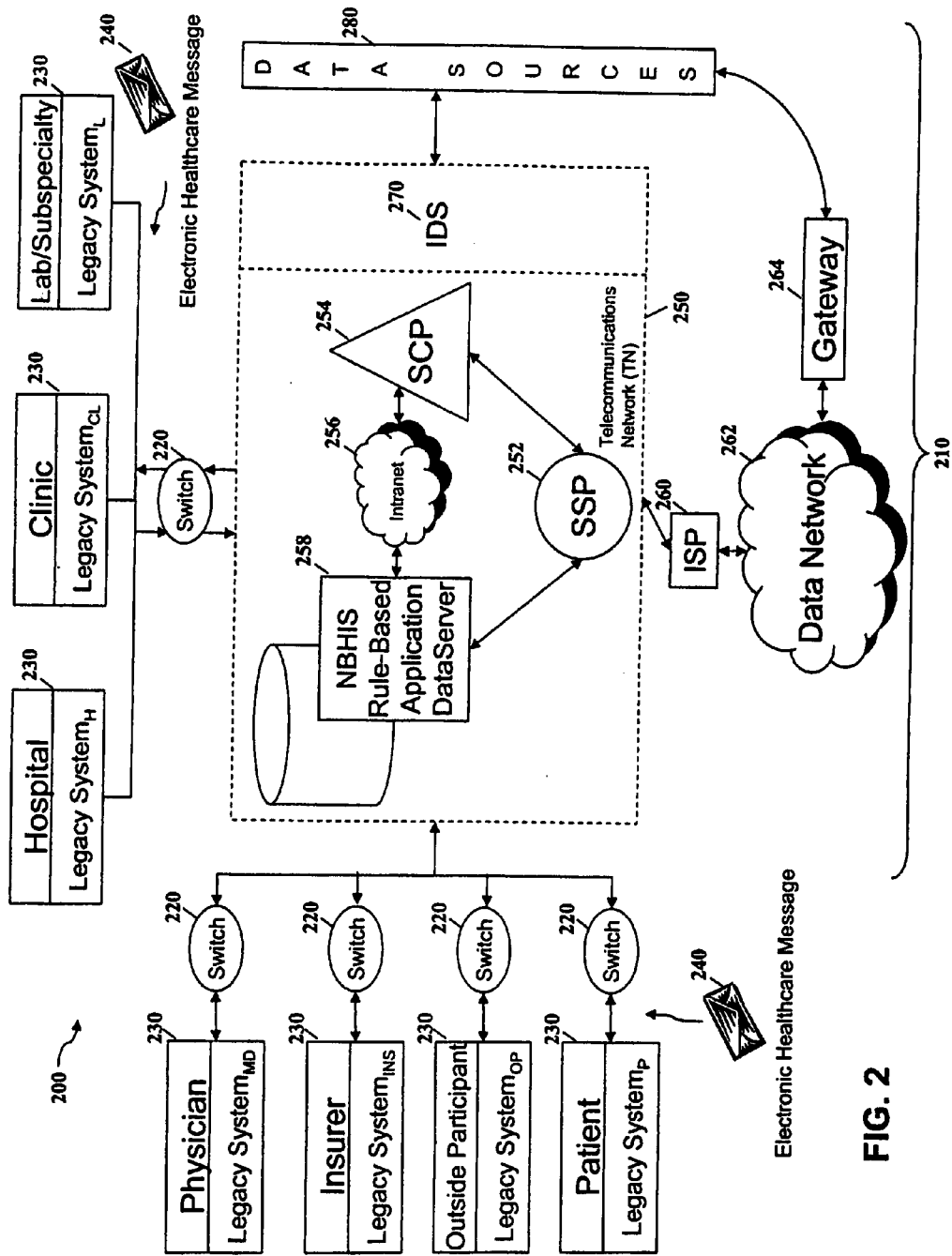
FIG. 2 is a schematic showing an exemplary operating environment for a telecommunications network-based healthcare information system according to an embodiment of this invention.

FIG. 2 is a schematic showing an exemplary operating environment for a telecommunications network-based healthcare information system (NBHIS) 200. The NBHIS 200 includes a shared, interconnected network 210 of one or more switches 220 that provide access points of presence for one or more legacy systems 230. Each legacy system 230 includes at least one computer system 100 having the NBHIS Management Module 110 (including the IP address or other communications address associated with a participant's telecommunications network and/or data network connection) residing within the computer system 100, a telecommunications network 250 typically including a service switching point (SSP) 252, a service control point (SCP) 254, an Intranet 256, and a NBHIS Rule-Based Application Dataserver 258, an Internet Service Provider (e.g., America On-Line) 260, a data network 262, a gateway 264, an Integrated Delivery System (IDS) 270, and external data sources 280. Each switch 220 allows the connected legacy systems 230 to communicate electronic healthcare messages 240 via the telecommunications network facility 250, such as, for example, a central office (CO), a mobile telephone switching office (MTSO), and/or a combination CO/MTSO. The telecommunications network facility 250 may use any means of coupling one switch 220 to the telecommunications network facility 250, but the coupling means is preferably high-capacity, high-bandwidth optical transport services, Gigabit Ethernet services, and/or the like. As those of ordinary skill in the art of telecommunications understand, the telecommunications network facility 250 could also link each switch 220 via other appropriate means, such as, for example a Synchronous Optical Network (SONET) structure with redundant, multiple rings.

Typically, a customer and/or user of the NBHIS Management Services uses the computer system 100 to gain access to the NBHIS 200. For example, if a user wishes to send, receive, or access voice, video, and/or data (e.g., read and respond to e-mail, order test results, view video-clips including static images, listen to recorded information, engage in an interactive-diagnosis session, etc.), then the computer system 100 connects with the interconnected network 210 via switch 220. Each electronic healthcare message 240 sent from a computer system 100 of the participant's legacy system 230 is routed through the telecommunications network 250 via switch 220. Communications signals associated with the address of the electronic healthcare message 240 arrive at SSP 252 that analyzes the signals and determines whether the electronic healthcare message 240 is addressed to another NBHIS participant. Depending on the address and content of the electronic healthcare message (e.g., whether or not the electronic healthcare message is to a non-participant, whether or not an object is attached, etc.), the SSP 252 may route the electronic healthcare message immediately over the telecommunications network 250 to attempt a connection or the SSP may communicate with SCP 254 for further electronic healthcare message processing and routing information (including eventual routing to the NBHIS Rule-Based Application DataServer 258 if the electronic healthcare message 240 is to another NBHIS participant). The NBHIS 200 may include wired, optical, and/or wireless elements and may further include private network elements, such as private branch exchanges (PBXs), and/or other elements (not shown). The telecommunications network 250 includes Advanced Intelligent Network (AIN) componentry controlling many features of the network. The telecommunications network 250 or switch 220 could also include a packet-based "soft switch" that uses software control to provide voice, video, and/or data services by dynamically changing its connection data rates and protocols types. If the telecommunications network 250 or switch 220 should include a softswitch, the AIN componentry is replaced by an application server that interfaces with the softswitch via a packet protocol, such as Session Initiation Protocol (SIP). The signaling between the computer system 100, the switch 220, the telecommunications network 250 including AIN componentry, and the data network 262, however, are well understood in by those of ordinary skill the art and will not be further described. Further, those of ordinary skill in the art will be able to apply the principles of this invention to their own legacy systems including their network configurations which may differ substantially from the telecommunications system shown in the figures.

The NBHIS Rule-Based Application Dataserver 258 communicates with SCP 254 and Intranet 256 to effectively provide NBHIS Management Services. These NBHIS Management Services allow a NBHIS participant to control access, sharing, notification, routing, security, transactions, troubleshooting, management, and/or additional processing of electronic healthcare messages exchanged to/from other NBHIS participants. For example, NBHIS Management Services allows a user to control how the object is processed into the receiver legacy system including (i) sending the object to a storage device associated with the telecommunications service provider, (ii) archiving the object, (iii) encrypting the object, (iv) copying the object, and (v) associating the object with related electronic healthcare data in the receiver legacy system. Further, the NBHIS Management Services may be activated, de-activated, administered, and/or otherwise managed by the user or another entity with authorization (e.g., telecommunications service provider). Thus, NBHIS Rule-Based Application Dataserver 258 functions as a computer server, database, and processor that is dedicated to managing NBHIS participant activity including their communication of electronic healthcare messages over the interconnected network 210. In an embodiment, the NBHIS Rule-Based Application Dataserver 258 has the ability to communicate with the data network 262 using standard transmission control protocol and Internet protocol (TCP/IP) or other appropriate protocols. Further, the NBHIS Management Module 110, may be downloaded from ISP 260, NBHIS Rule-Based Application Dataserver 258, Intranet 256, or provided on a storage media (e.g., diskette, CD-ROM, or installed by the computer system manufacturer) to a subscribing customer or user to install on the computer system 100 to enable, disable, and further control a variety of the NBHIS Management Services.

Figure 3:
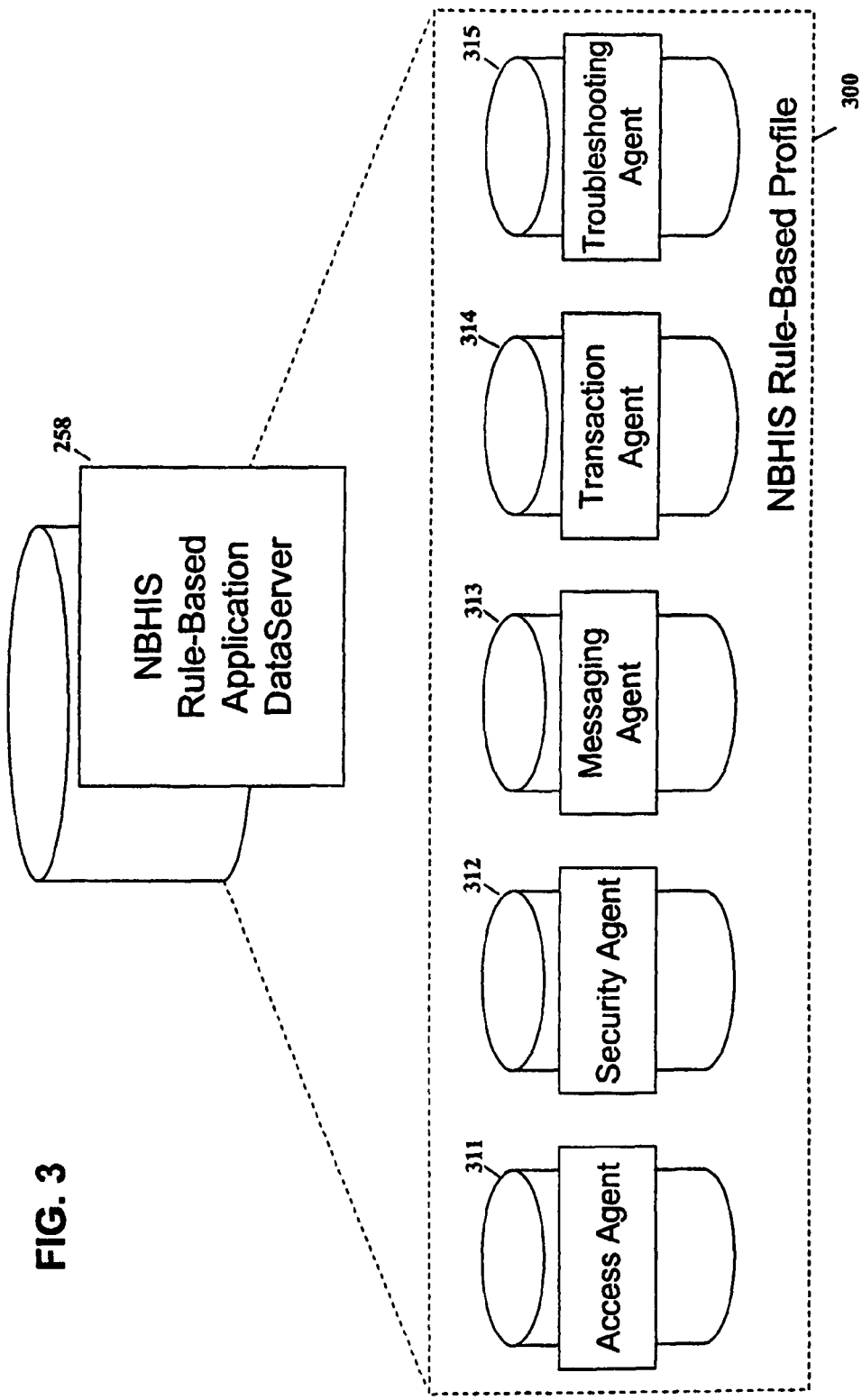
FIG. 3 is a more detailed schematic of a rule-based application dataserver shown in FIG. 2.

Referring now to FIG. 3, the participant interacts with the NBHIS Management Module 110 and with Intranet 256 to access and login to the NBHIS Rule-Based Application DataServer 258 and to establish the NBHIS Rule-Based Profile 300. The NBHIS Rule-Based Application Dataserver 258 stores one or more NBHIS Rule-Based Profiles 300 that include data and applications associated with an Access Agent 311, a Security Agent 312, a Messaging Agent 313, a Transaction Agent, and a Troubleshooting Agent 315. For example, the Access Agent 311, Security Agent 312, Messaging Agent 313, Transaction Agent, and Troubleshooting Agent 315 may contain a variety of fields and/or files associated with at least one of the following: login information associated with a participant, password entered by the participant, telephone number or Service Node of the participant (this may include a plurality of addresses that are associated with a Service Node or other switch serving the legacy system), TCP/IP address of the participant, profile of the computer system 100 or other communications device associated with the incoming electronic healthcare message (e.g., presentation formats for various communications devices), a time or date identifier (e.g., day of week or calendar date), other information associated with the communications signal, size and content of electronic healthcare message (including types of files that are transmitted as an attached object), transaction reply(s), transaction notification(s), display of a GUI (e.g., color, font, placement of NBHIS Management Module on screen, etc.), NBHIS Management Service defaults (e.g., whether the IDS automatically re-formats the attached object to a compatible object and updates the receiving legacy system with the compatible object), and other selections related to NBHIS Management Services, such as electronic healthcare message features, electronic healthcare message routing, and troubleshooting problems or error messages.

Figure 4:
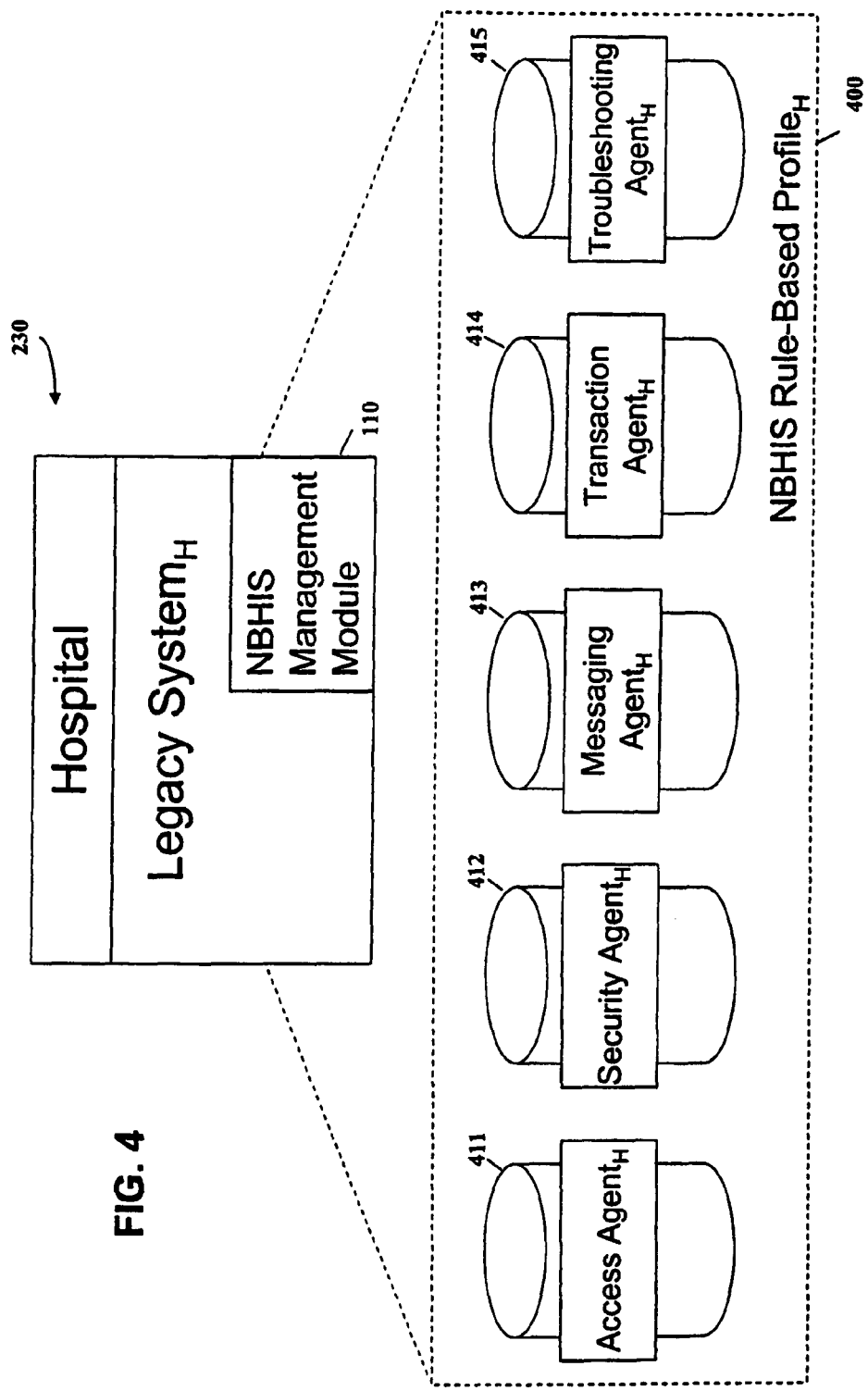
FIG. 4 is a more detailed schematic of a hospital's legacy system shown in FIG. 2.

FIG. 4 illustrates an embodiment of establishing a local NBHIS Rule-Based Profile 400 to interact with the NBHIS Rule-Based Profile of the interconnected network 210. The NBHIS Management Module 110 of computer system 100 is used to establish, store, and manage the NBHIS Rule-Based Profile 400 for legacy system (i.e., the hospital's legacy system). The legacy system stores one or more NBHIS Rule-Based Profiles 400 that include data and applications similar to NBHIS Rule-Based Profiles 300. The NBHIS Rule-Based Profiles 400 provide increased security by allowing the participant to internally control electronic information, utilize existing databases to add, delete, or otherwise change electronic information, control how the participant's legacy system interacts with the IDS, and control routing instructions within its legacy system.

Figure 5:
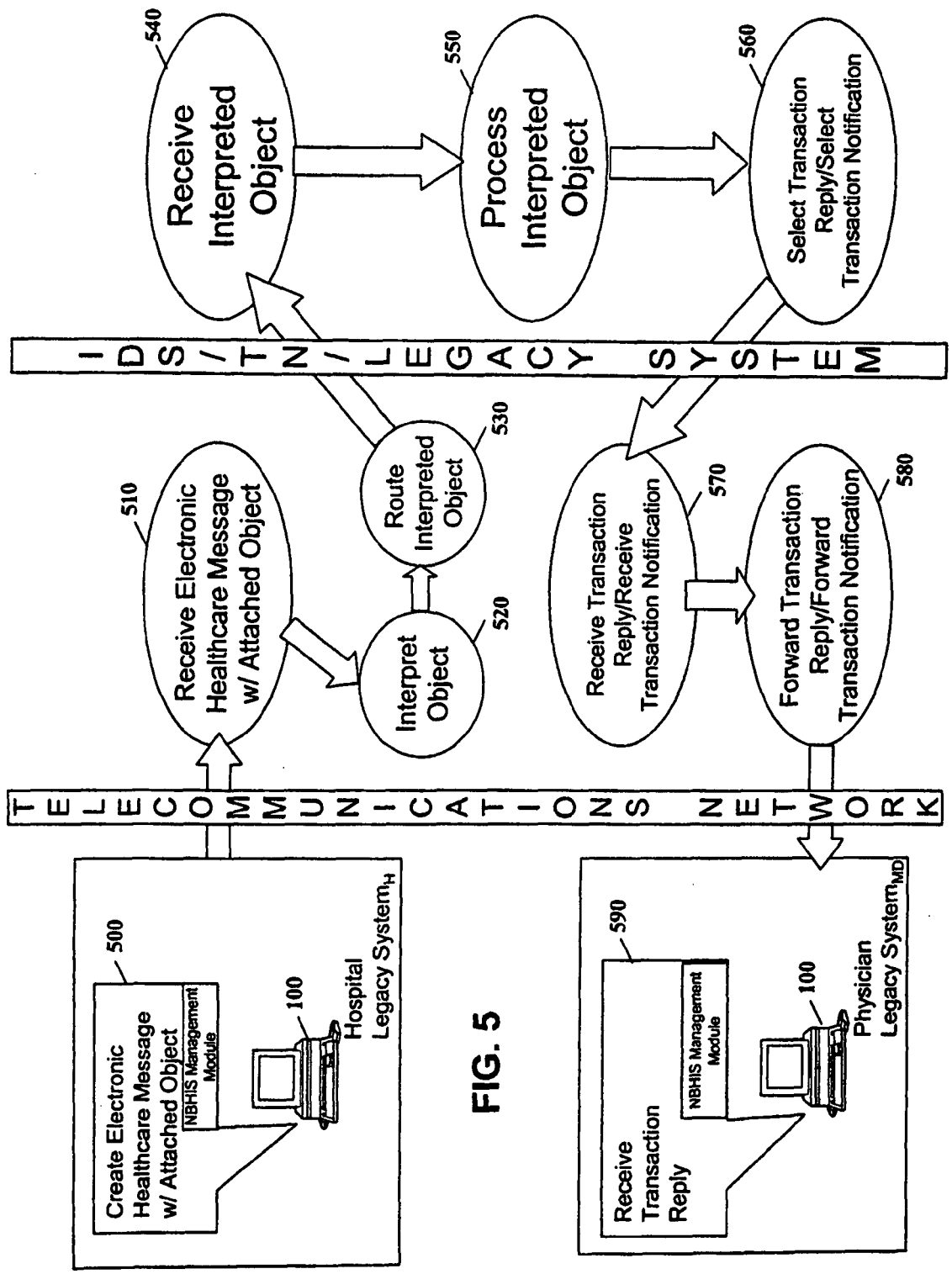
FIG. 5 is a schematic showing an exemplary framework for the flow of electronic healthcare message through the telecommunications network-based healthcare information system according to an embodiment of this invention.

FIG. 5 is a schematic showing an exemplary framework for the flow of the electronic healthcare message 240 through the NBHIS 200. Typically, the flow of the electronic healthcare message 240 involves the participant using the computer system 100 to create the electronic healthcare message 240 with an attached object (step 500). The participant may create the electronic healthcare message 240 using a variety of software applications including electronic messaging, word processing, and others (e.g., MICROSOFT OUTLOOK® and MICROSOFT WORD® are registered trademarks of Microsoft Corporation, One Microsoft Way, Redmond Wash. 98052-6399, 425.882.8080, www.Microsoft.com). Alternatively, the electronic healthcare message 240 may be created using the NBHIS Management Module 110 that includes instructions to/for the IDS 270. The electronic healthcare message 240 is routed and received in the telecommunications network 250 (step 510). In an embodiment, the NBHIS Rule-Based DataServer 258 determines whether external data sources 280 need to be queried for related electronic healthcare data or for retrieving an object that is linked rather than attached to the electronic healthcare message. Next, the telecommunications network 250 interprets the electronic healthcare message including the attached object, related healthcare data, and/or the linked object (step 520) using network elements including the NBHIS Rule-Based Application DataServer 258. Thereafter, the NBHIS Rule-Based Application DataServer 258 routes the object (e.g., the attached object, related healthcare data, and/or the linked object) to the IDS 270 so that the object may be interpreted from the sending participant's legacy system for compatible exchange with the receiving participant's legacy system (i.e., from the hospital's legacy system to the physician's legacy system) (step 530). The IDS 270 may be a stand alone system (not shown in the figures), the IDS 270 may be integrated into the telecommunications network 250 (as shown in FIG. 2), the IDS 270 may be integrated with one of the participant's legacy systems (not shown in the figures) that is accessed by the telecommunications network 250 or data network 262, or the IDS 270 may be a combination of these systems (not shown). No matter how the IDS 270 is deployed, the interpreted object is received (step 540), processed so that the object is compatible for the receiving legacy system (step 550), and associated with a transaction reply (e.g., a communication to the receiving participant about the electronic healthcare message including information about the attached object or the compatible object) or with a transaction notification (e.g., a communication to the sending participant about the electronic healthcare message including information about the attached object or the compatible object) (step 560).

Thereafter, the transaction reply and/or the transaction notification are routed through the telecommunications network 250 (step 570) and forwarded to the receiving legacy system (step 580) or to the sending legacy system (not shown). The NBHIS Management Module 110 presents the electronic healthcare message 240 so that the receiving participant of the computer system 100 has immediate access, notification, and management of the electronic healthcare message 240 including the compatible object and updated data in the receiving legacy system.

Figure 6:
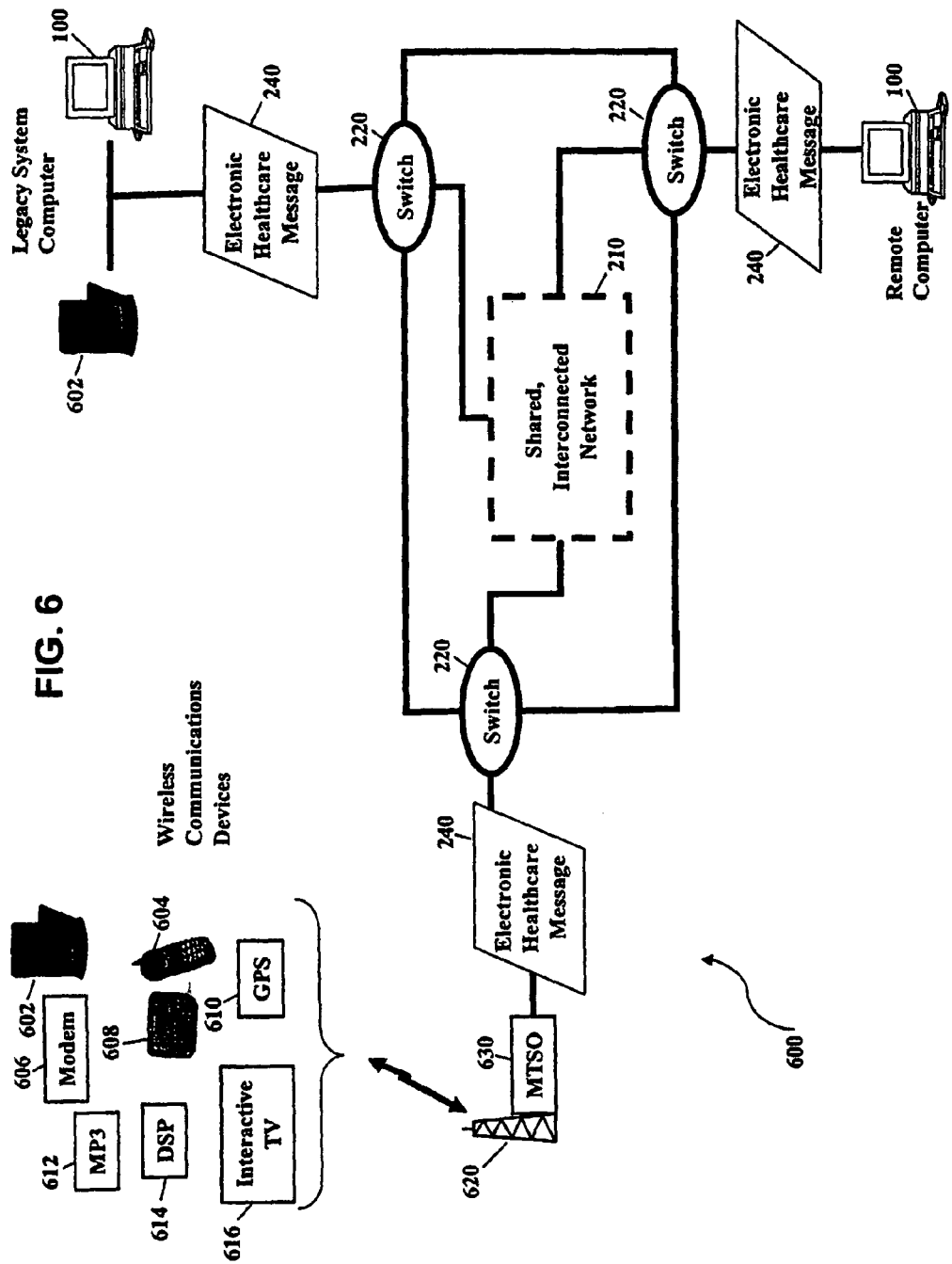
FIG. 6 is a schematic showing an exemplary embodiment of communicating an electronic healthcare message using wired and wireless communications devices associated with the telecommunications network-based healthcare information system according to an embodiment of this invention.
Figure 7:
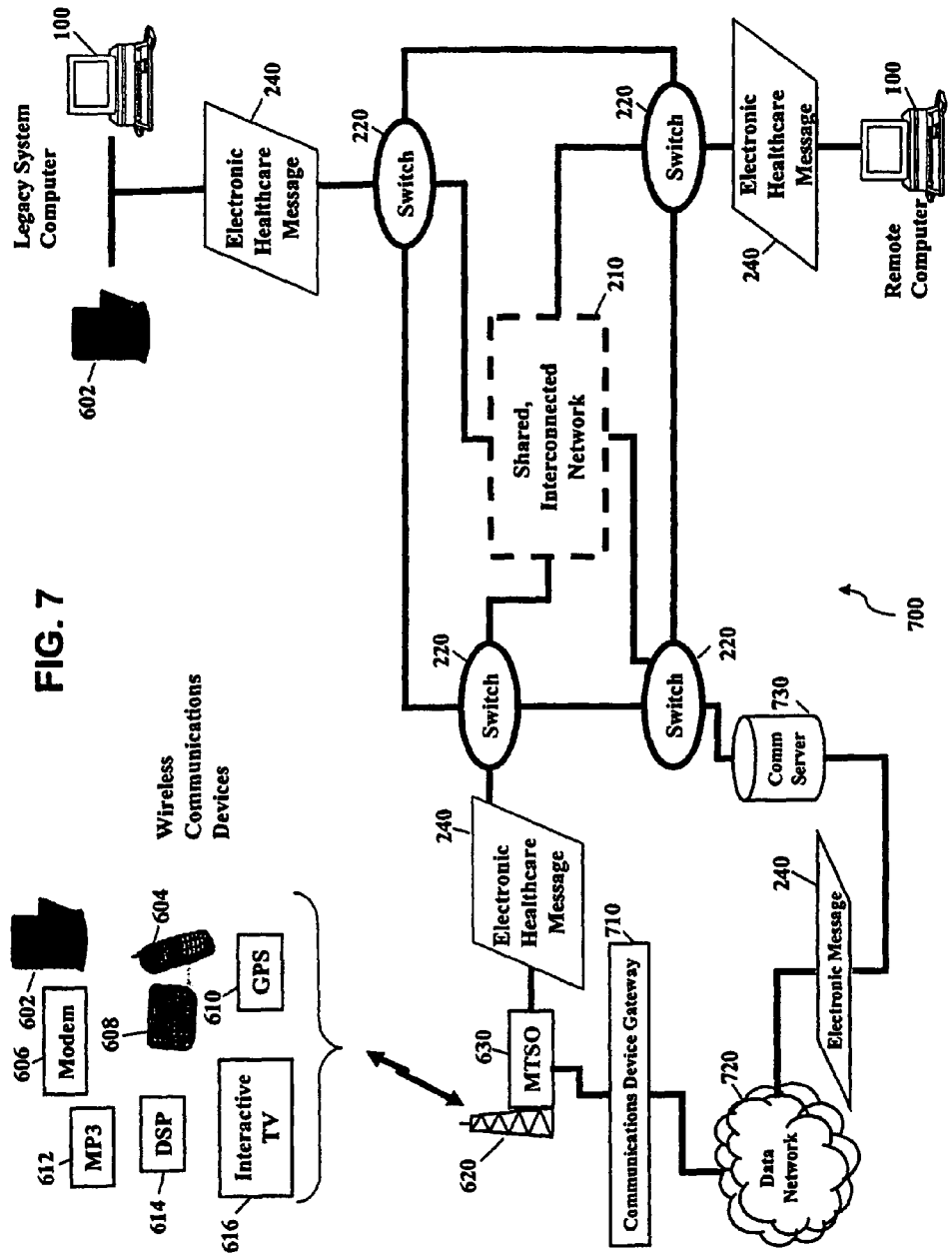
FIG. 7 is a schematic showing another exemplary embodiment of communicating an electronic healthcare message using wired and wireless communications devices associated with the telecommunications network-based healthcare information system according to an embodiment of this invention.

FIGS. 6-7 are schematics showing a variety of wired and wireless communications devices communicating the electronic healthcare message 240 through the shared, interconnected network 210 according to alternate embodiments of this invention. The means of coupling the computer system 100 or other communications device (shown as reference numerals 602-616) to the switch 220 include a variety of means, including optical transmission of electronic healthcare data, wireless transmission of electronic healthcare data, and/or fixed-wire transmission of electronic healthcare data (e.g., via a local loop of a telecommunications network to communicate electronic healthcare data). Fiber optic technologies, spectrum multiplexing (such as Dense Wave Division Multiplexing), Ethernet and Gigabit Ethernet services, and Digital Subscriber Lines (DSL) are just some examples of the coupling means.

FIG. 6 illustrates a telecommunications network-based healthcare information system 600 similar to the telecommunications system disclosed in FIG. 2; however, telecommunications network-based healthcare information system 600 illustrates an embodiment of the call flow for alternate communications devices. Telecommunications system 600 includes alternate communications devices that include a personal digital assistant (PDA) 602, an IP cellular phone 604, a modem 606, an interactive pager 608, a global positioning system transceiver 610, an MP3 player 612, a digital signal processor (DSP) 614, and an interactive television 616. These alternate communications devices communicate via an antenna 620 communicating with an MTSO 630 that transmits the electronic healthcare message 240 to the switch 220. Switch 220 routes the electronic healthcare message 240 to the shared, interconnected network 210. In addition, FIG. 6 illustrates that the computer systems of the legacy system include a variety of communications devices including personal computer systems 100 and wireless communications devices, such as PDA 602. Alternatively, a remote computer system, such as personal computer system 100, may also connect to the shared, interconnected network 210 (typically via a modem connection (not shown)). Regardless of the communications device used to send the electronic healthcare messages 240, the electronic healthcare messages 240 may need to be formatted accordingly for the receiving communications device (including audio, text (e.g., ASCII), video, other digital formats, and combination thereof). Thus, the NBHIS Rule-Based Application DataServer 258 has the intelligence to associate the presentation capabilities of the alternate communications device.

FIG. 7 illustrates a telecommunications network-based healthcare information system 700 similar to the telecommunications system disclosed in FIG. 6; however, telecommunications network-based healthcare information system 700 includes a communications device gateway 710 connected with a data network 720 and a communications server 730 so that the electronic healthcare message communicated to/from switch 220 may be appropriately formatted for presentation on alternate communications devices 602-616. For example, if the alternate communications device uses the Wireless Application Protocol (WAP) technique, then the electronic healthcare message 240 is communicated to a communications ("Comm") server 730. The communications server 730 formats the electronic healthcare message 240 into one or more Wireless Mark-up Language (WML) messages that are communicated over a data network 720 to a communications device gateway 710. The communications device gateway 710 then interfaces with the MTSO 630, and the MTSO 630 then wirelessly communicates the electronic healthcare message to the pager 608 or the wireless personal data assistant 604 (or a WAP phone). The Wireless Mark-up Language (WML) and the WAP technique are known and will not be further described. This is a description of a solution for a specific wireless protocol, such as WAP. This solution may be clearly extended to other wireless protocol, such as i-mode, VoiceXML (Voice eXtensible Markup Language), Dual Tone Multi-Frequency (DTMF), and other signaling means.

Figure 8:
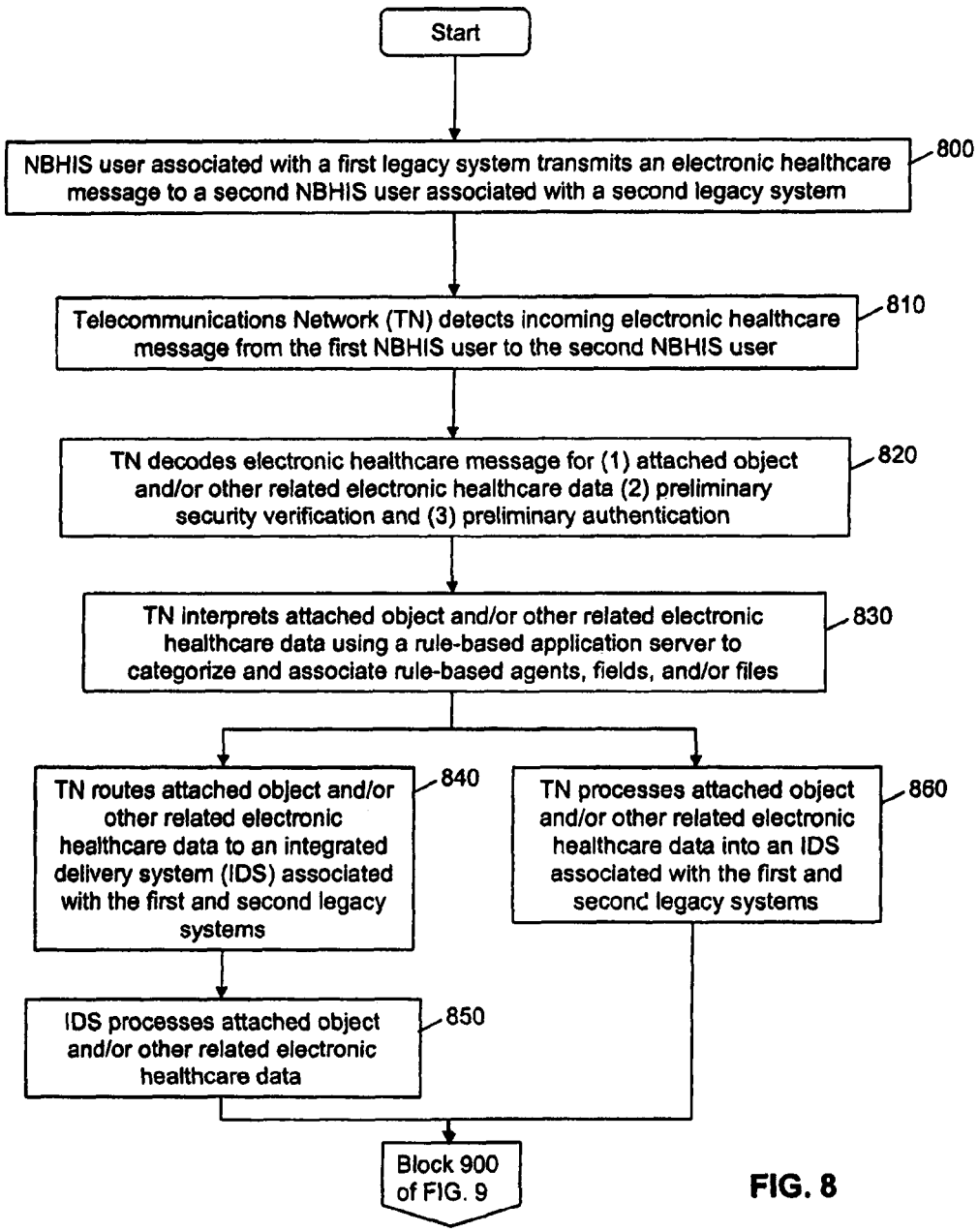
FIGS. 8-9 are flowcharts showing a method of providing the telecommunications network-based healthcare information system service to a customer according to an embodiment of this invention.
Figure 9:
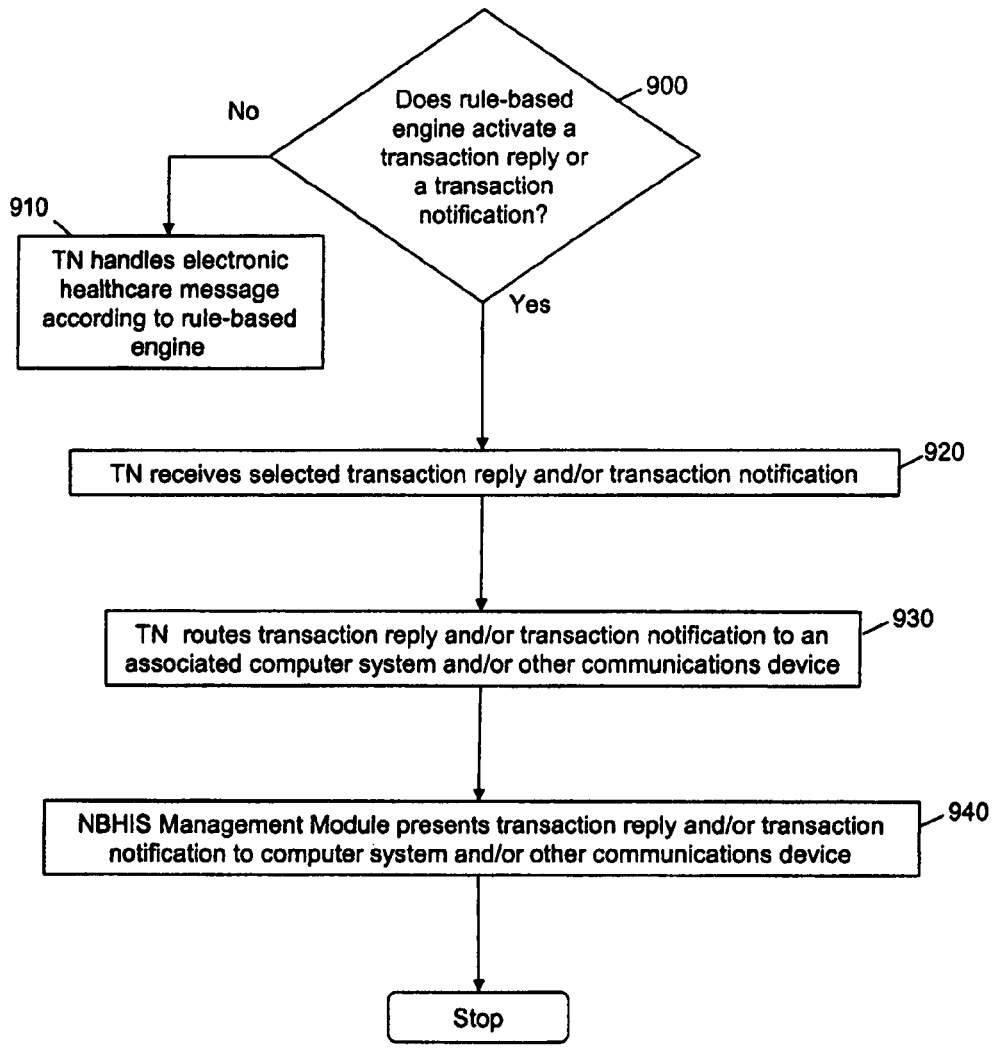

FIGS. 8-9 illustrate a flowchart showing an overview of a process of providing the telecommunications network-based healthcare information system service to a customer according to an embodiment of this invention. While the process in FIGS. 8-9 are shown in series, these processes may occur in different orders and/or at simultaneous times as one of ordinary skill in the art will understand.

Referring now to FIG. 8, a NBHIS participant (e.g., a user) associated with a first legacy system transmits an electronic healthcare message to a second NBHIS participant associated with a second legacy system (block 800). A telecommunications network (TN) detects an incoming electronic healthcare message from the first NBHIS user to the second NBHIS user (block 810). The telecommunications network decodes the incoming electronic healthcare message for (1) an attached object and/or other related electronic healthcare data between legacy systems (e.g., queried data from an external data source 280, a linked object, data that is cut and pasted into the body of an email, etc.), (2) preliminary security verification, and (3) preliminary authentication (e.g., data and/or participants may be authenticated) (block 820). Next, the telecommunications network interprets the attached object and/or other related electronic healthcare data using a rule-based application server (e.g., NBHIS Rule-Based Application DataServer shown as reference numeral 258 in FIG. 2) to categorize and associate rule based agents, fields, and/or files (block 830). The attached object and/or other related electronic healthcare data is then processed according to how an Integrated Delivery System (IDS) is configured (e.g., integrated into the telecommunications network or accessed separate from the telecommunications network). If the integrated delivery system is not integrated with the telecommunications network (e.g., the integrated delivery system is accessed separate from the telecommunications network), then the telecommunications network routes the attached object and/or other related electronic healthcare data to the integrated delivery system associated with the first and the second legacy systems (block 840), and the integrated delivery system processes the attached object and/or other related electronic healthcare data so that the attached object and/or other related electronic healthcare data can be exchanged between legacy systems (block 850). If the integrated delivery system is integrated with the telecommunications network, then the telecommunications network processes the attached object and/or other related electronic healthcare data into the integrated delivery system so that the attached object and/or related electronic healthcare data can be exchanged between the first and the second legacy systems (block 860).

By allowing both IDS architects, NBHIS Management Services may be dynamically implemented across different platforms.

The method then continues with block 900 of FIG. 9. The rule based engine determines whether to activate a transaction reply and/or a transaction notification (block 900). If there is no transaction reply and/or no transaction notification, then the telecommunications network handles the electronic healthcare message and/or other related electronic healthcare data according to instructions from the rule-based engine (block 910). Alternatively, if a transaction replay and/or transaction notification is activated, then the telecommunications network selects the appropriate transaction reply and/or transaction notification (block 920), routes the transaction replay and/or transaction notification to a computer system or other communications device (block 930), and a client application (e.g., NBHIS Management Module 110) residing on the computer system or other communications device presents the transaction reply and/or transaction notification (block 940).

While several exemplary implementations of embodiments of this invention are described herein, various modifications and alternate embodiments will occur to those of ordinary skill in the art. Accordingly, this invention is intended to include those other variations, modifications, and alternate embodiments that adhere to the spirit and scope of this invention.

What is claimed is:

1. A method, comprising:
   receiving an electronic message identifying a sender's address and a recipient's address;
   comparing the sender's address and the recipient's address to addresses associated with a private data network;
   routing the electronic message entirely within the private data network in response to both the sender's address and the recipient's address matching the addresses associated with the private data network; and
   routing the electronic message to a public data network in response to at least one of the sender's address and the recipient's address not matching the addresses associated with the private data network.

2. The method of claim 1, further comprising receiving an object associated with the electronic message.

3. The method of claim 2, further comprising categorizing the object.

4. The method of claim 2, further comprising converting the object from a format to another format.

5. The method of claim 2, further comprising postponing a conversion of the object.

6. The method of claim 1, further comprising processing a reply to the electronic message.

7. The method of claim 1, further comprising selecting a reply for delivery to the sender's address.

8. The method of claim 1, further comprising selecting a notification for delivery to the recipient's address.

9. The method of claim 2, further comprising converting the object into a format compatible with an end user's system.

10. The method of claim 1, further comprising integrating telephony events with at least one of the sender's address and the recipient's address.

11. The method of claim 2, further comprising declining to convert the object from a format to another format.

12. A system, comprising:
   a processor; and
   memory storing code that when executed causes the processor to perform operations, the operations comprising:
   receiving an electronic message identifying a sender's address and a recipient's address;
   comparing the sender's address and the recipient's address to addresses associated with a private data network;
   routing the electronic message entirely within the private data network in response to both the sender's address and the recipient's address matching the addresses associated with the private data network; and
   routing the electronic message to a public data network in response to at least one of the sender's address and the recipient's address fails to match the addresses associated with the private data network.

13. The system of claim 12, wherein the operations further comprise receiving an object associated with the electronic message.

14. The system of claim 13, wherein the operations further comprise categorizing the object.

15. The system of claim 13, wherein the operations further comprise converting the object from a format to another format.

16. The system of claim 13, wherein the operations further comprise postponing a conversion of the object.

17. A memory storing instructions that when executed cause a processor to perform operations, the operations comprising:
   receiving an electronic message identifying a sender's address and a recipient's address;
   comparing the sender's address and the recipient's address to addresses associated with a private data network;
   routing the electronic message entirely within the private data network in response to both the sender's address and the recipient's address matching the addresses associated with the private data network; and
   routing the electronic message to a public data network in response to at least one of the sender's address and the recipient's address failing to match the addresses associated with the private data network.

18. The memory of claim 17, wherein the operations further comprise receiving an object associated with the electronic message.

19. The memory of claim 18, wherein the operations further comprise categorizing the object.

20. The memory of claim 18, wherein the operations further comprise converting the object from a format to another format.

* * * * *